United States Patent
Stough

(10) Patent No.: US 6,585,742 B2
(45) Date of Patent: Jul. 1, 2003

(54) WART REMOVAL METHOD AND DEVICE

(76) Inventor: Dowling B. Stough, One Mercy La., Suite 304, Hot Springs, AR (US) 71913

( * ) Notice: Subject to any disclaimer, the term of this patent is extended or adjusted under 35 U.S.C. 154(b) by 80 days.

(21) Appl. No.: 09/851,477

(22) Filed: May 8, 2001

(65) Prior Publication Data

US 2002/0169462 A1 Nov. 14, 2002

(51) Int. Cl.$^7$ ................................................ A61F 29/04
(52) U.S. Cl. ........................... 606/131; 15/142; 15/128; 15/236.06; 15/238.08
(58) Field of Search .......................... 606/131; 132/141, 132/142, 150, 152, 901, 126; 119/602, 603, 664; 15/142, 151, 186–188, 236.05, 236.06, 236.08

(56) References Cited

U.S. PATENT DOCUMENTS

| | | | |
|---|---|---|---|
| 132,468 A | | 10/1872 | Jacobsohn |
| 243,671 A | | 6/1881 | Wilson |
| 408,926 A | | 8/1889 | Palmer |
| 930,678 A | * | 8/1909 | Moore .......................... 132/126 |
| 1,113,054 A | * | 10/1914 | Sadler ....................... 15/104.94 |
| 1,471,527 A | * | 10/1923 | Proctor ........................ 132/117 |
| 1,711,486 A | * | 5/1929 | Bushman ..................... 132/142 |
| 2,154,846 A | * | 4/1939 | Heymann et al. .............. 15/110 |
| 3,107,665 A | * | 10/1963 | Nordgren ..................... 119/632 |
| 3,133,546 A | * | 5/1964 | Dent .......................... 119/612 |
| 3,468,079 A | * | 9/1969 | Kaufman ................. 407/29.13 |
| 4,397,325 A | | 8/1983 | Van Roeyen |
| 4,595,591 A | | 6/1986 | Mardi et al. |
| 5,091,171 A | | 2/1992 | Yu et al. |
| 5,151,415 A | | 9/1992 | Sirany |
| 5,476,664 A | | 12/1995 | Robinson et al. |
| 5,561,157 A | | 10/1996 | Yu et al. |
| 5,626,099 A | * | 5/1997 | Staller et al. ................ 119/600 |
| 5,665,776 A | | 9/1997 | Yu et al. |
| 5,800,446 A | | 9/1998 | Banuchi |
| 5,817,114 A | | 10/1998 | Anderson et al. |
| 5,845,603 A | * | 12/1998 | Efaw ........................... 119/605 |
| 5,884,633 A | * | 3/1999 | Ford ........................... 132/137 |
| 5,997,549 A | | 12/1999 | Sauceda et al. |
| 6,017,351 A | | 1/2000 | Street |
| 6,191,167 B1 | | 2/2001 | Yu et al. |
| 6,257,172 B1 | * | 7/2001 | Leppanen .................... 119/605 |

OTHER PUBLICATIONS

Van Scott, Yu, Alpha hydroxy acids: procedures for use in clinical practice, Cutis 1989, Mar.; 43(3):222–8.

Halasz, Treatment of warts with topical pyruvic acid: with and without added 5–fluorouracil, Cutis 1998, Dec.; 62(6):283–5.

Van Scott, Yu, Control of keratinization with alpha–hydroxy acids and related compounds: topical treatment of ichthyotic disorders, 1974, Oct.; 110(4):586–90.

* cited by examiner

Primary Examiner—Kevin Shaver
Assistant Examiner—Michael B. Priddy
(74) Attorney, Agent, or Firm—Mark A. Rogers; Gary N. Speed

(57) ABSTRACT

A wart removal device includes a handle and a pad. The pad has a base and tines with each tine preferably having a height not less than approximately twice its width. The tine height is preferably less than approximately 0.1 inch. The pad has a width that is preferably not greater than approximately ¼ inch and a length that is preferably not less than approximately twice its width. Each tine is sharpened so that opposing sides form a point at an upper edge with the opposing sides forming an angle of from approximately 20° to approximately 40°. In operation, the device is raked against wart tissue to create incisions in the wart tissue. The sharpness and cutting depth of the device are designed to create incisions without causing noticeable bleeding. The device may be provided in a kit with a medicament, such as pyruvic acid, to improve the effectiveness of the medicament.

5 Claims, 2 Drawing Sheets

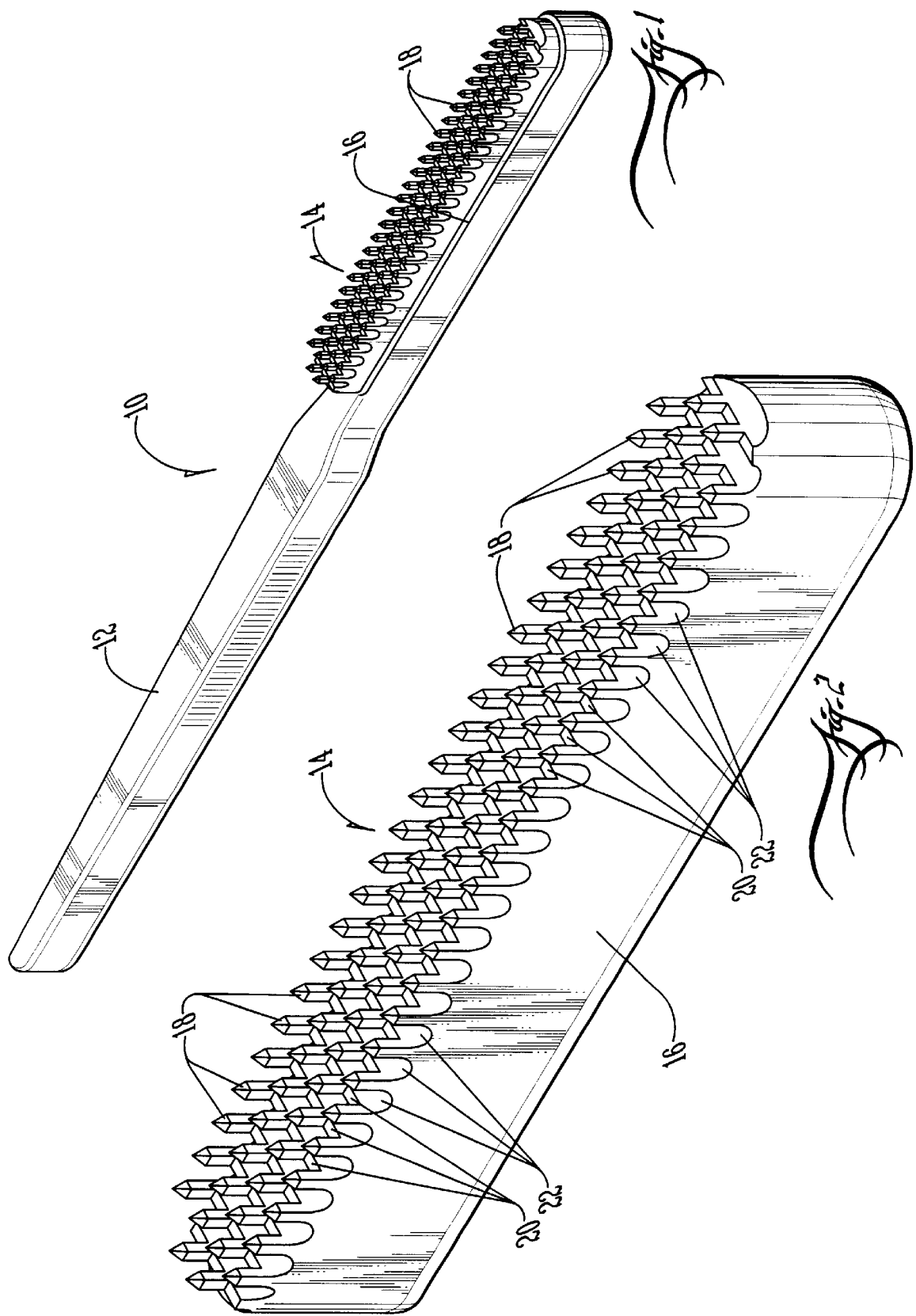

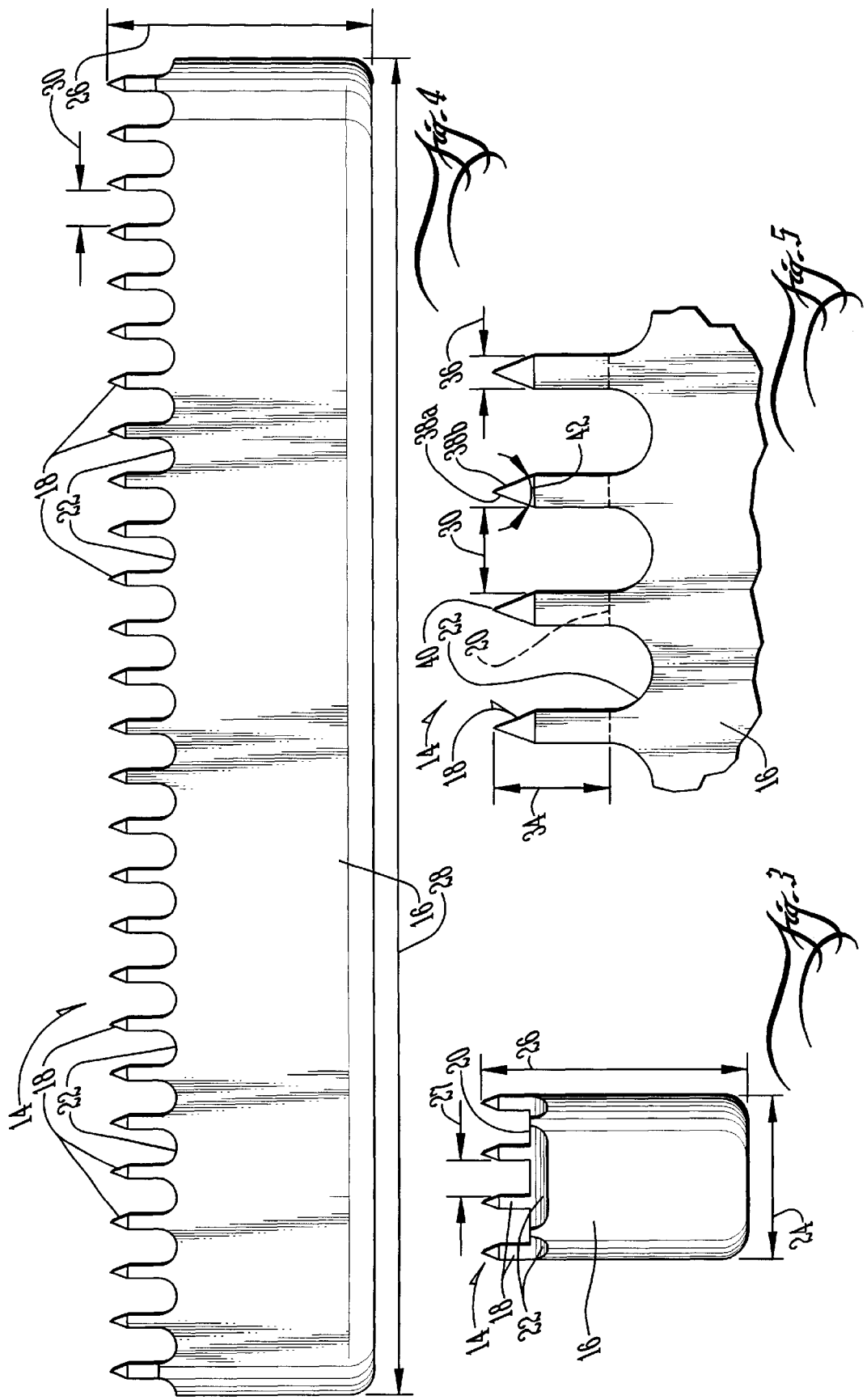

WART REMOVAL METHOD AND DEVICE

BACKGROUND OF THE INVENTION

This invention relates to wart removal, and more particularly to a method and device for accomplishing wart removal.

A wart is a papillomatous growth characterized by a relatively thick, tough, keratinous outer layer. It is believed that a virus causes warts. A wide variety of wart removal techniques are known in the art. Wart removal techniques include burning and freezing. These techniques must typically be performed by a physician in a clinical setting. Various lotions and medicaments have been developed for topical application. Still, it is difficult to identify a lotion or medicament that is safe for a patient to use at home and that is still able to penetrate the relatively thick, tough, keratinous outer layer of a wart. Physicians have used scalpels and razors to remove warts by cutting or paring. A variety of tools or devices have also been proposed that use roughened surfaces to remove wart tissue over a period of days or weeks by rubbing or abrading. Cutting or paring a wart with a scalpel or razor generally provides superior results as compared to rubbing or abrading a wart with a roughened surface. Still, it is inconvenient and costly for a patient to make repeated trips to a physician for frequent cutting or paring treatments. For obvious safety reasons, physicians and patients are reluctant to have the patient use a scalpel or razor for repeated cutting and paring at home. Nonetheless, using a roughened surface to slowly rub or abrade wart tissue leaves much to be desired. For example, the roughened surfaces typically lack the cutting depth and sharpness to effectively penetrate the stratum corneum, the relatively thick, tough, keratinous outer layer of a wart.

SUMMARY OF THE INVENTION

It is therefore an object of the present invention to provide a wart removal method and device that allows a patient to safely and effectively remove wart tissue.

It is a further object of the present invention to provide a wart removal method and device of the above type that combines the advantages of clinical cutting or paring devices with the convenience of home treatment devices.

It is a still further object of the present invention to provide a method and device of the above type that allows a patient to safely cut away wart tissue without extensive training and without causing noticeable bleeding.

It is a still further object of the present invention to provide a method and device of the above type that allows a patient to safely cut away wart tissue in a specific, pinpointed location.

It is a still further object of the present invention to provide a method and device of the above type that allows a patient to safely use a kit to remove a wart in a non-clinical setting.

It is a still further object of the present invention to provide a device of the above type, and a method of using the same, that provides sufficient cutting depth and sharpness to penetrate the stratum corneum, the relatively thick, tough, keratinous outer layer of a wart and that is still safe for a patient to use in a non-clinical setting.

It is a still further object of the present invention to provide a method and device of the above type that increases the effectiveness of a medicament by allowing a patient to make incisions through the relatively thick, toughened, keratinous outer layer of a wart prior to applying the medicament in a non-clinical setting.

Toward the fulfillment of these and other objects and advantages, a device and method of using same are disclosed. The device has a handle and a pad affixed to the handle. The pad has a base and a plurality of tines. Each tine preferably has a height that is not less than approximately twice its width and that is more preferably not less than approximately three times its width. The tine height is preferably less than approximately 0.1 inch and is more preferably less than approximately 0.05 inch. The pad has a width that is preferably not greater than approximately ¼ inch and a length that is preferably not less than approximately twice its width. The pad has a width that is more preferably not greater than approximately ⅛ inch and a length that is more preferably not less than approximately ½ inch. Each tine is preferably sharpened so that opposing sides form a point at an upper edge with the opposing sides forming an angle that is substantially within a range of from approximately 20° to approximately 40°. In operation, the device is raked against wart tissue to create a plurality of incisions in the wart tissue. The sharpness and cutting depth of the device are designed to create a plurality of incisions without causing noticeable bleeding. The device may be used in combination with a medicament, such as pyruvic acid, to improve the effectiveness of the medicament. The device and medicament may be provided as a kit, such as by prescription, for use by a patient in a non-clinical setting.

BRIEF DESCRIPTION OF THE DRAWINGS

The above brief description, as well as further objects, features and advantages of the present invention will be more fully appreciated by reference to the following detailed description of the presently preferred but nonetheless illustrative embodiments in accordance with the present invention when taken in conjunction with the accompanying drawings, wherein:

FIG. 1 is a perspective view of a device of the present invention;

FIG. 2 is an enlarged, elevation view of a pad of the present invention;

FIG. 3 is an enlarged, front elevation view of a pad of the present invention;

FIG. 4 is an enlarged, side elevation view of a pad of the present invention; and FIG. 5 is an enlarged sectional view of tines of the present invention.

DETAILED DESCRIPTION OF THE PREFERRED EMBODIMENT

Referring to FIG. 1, the reference numeral 10 refers in general to a wart removal device of the present invention. The device 10 comprises a handle 12 and a pad 14. The pad 14 comprises a base 16 and a plurality of tines 18.

The handle 12 is an elongate handle designed to be grasped by a user at a proximal end and having the pad 14 affixed to a distal end. The handle 12 is preferably plastic but may be made from any number of materials. It is preferred that the handle 12 be sufficiently rigid to allow it to hold the pad 14 in place during use. It is of course understood that the pad 14 may take any number of shapes, sizes, or configurations and that the handle 12 may be made from the same material as or formed integrally with the pad 14.

As best seen in FIG. 2, the pad 14 comprises a base 16 and a plurality of tines 18. The pad 14 is affixed to the handle 12 such as by using adhesives or by forming the pad into or as part of the handle. The tines 18 extend upward from the base 16 and are arranged to form a plurality of columns and a plurality of rows. The number of rows is preferably not less than approximately twice the number of columns and is more preferably not less than approximately four times the number of columns. The number of rows is preferably not less than 12, and the number of columns is preferably not greater than 6. In the preferred embodiment shown, the pad 14 has four columns of tines 18 and 27 rows of tines 18. The base 16 preferably provides substantially planar surfaces or ridges 20 that extend between the tines 18 in each row. Curved channels or troughs 22 may be formed in the base 16 between adjacent rows of tines 18. The pad 14 is preferably made from stainless steel but may be made from any number of materials.

As best seen in FIG. 3, the pad 14 has a width 24 that is preferably not greater than approximately ¼ inch, that is more preferably not greater than approximately ⅛ inch, and that is most preferably approximately 0.12 inch. The pad 14 has a height 26 that is preferably not greater than approximately ½ inch, that is more preferably not greater than approximately ¼ inch, and that is most preferably approximately 0.195 inch. Each column of tines 18 is preferably spaced from adjacent columns of tines. The spacing 27 between adjacent columns is preferably, approximately 0.028 inch. As best seen in FIG. 4, the pad 14 has a length 28 that is preferably not less than approximately twice the pad width 24, that is more preferably not less than ½ inch, and that is most preferably approximately 0.95 inch. As also shown in FIG. 4, each row of tines 18 is preferably spaced from adjacent rows of tines 18. The spacing 30 between rows is preferably, approximately 0.026 inch.

As best seen in FIG. 5, each tine 18 has a height 34 and a width 36 that is measured at or near where the tine 18 meets the base 16. The height 34 is preferably greater than the width 36, is more preferably not less than approximately twice the width 36, and is most preferably not less than approximately three times the width 36. The tine height 34 is preferably less than approximately 0.1 inch, is more preferably less than approximately 0.05 inch, and is most preferably approximately 0.034 inch. Each tine 18 is sharpened so that opposing sides 38a and 38b meet to form a point 40 at an upper edge, with the opposing sides forming an angle 42 that is preferably substantially within a range of from approximately 20° to approximately 40°, that is more preferably substantially within a range of from approximately 30° to approximately 40°, and that is most preferably approximately 39°. Each tine 18 is preferably sharpened so that front and rear surfaces of the tine form a point 40 at the upper edge, with the front and rear surfaces forming this angle 42 and so that opposing left and right side surfaces also form a point 40 at the upper edge, with the opposing left and right side surfaces forming this angle 42.

In operation, it is preferred to have a user soak the wart or area to be treated in water for approximately five to ten minutes to soften the keratin. Along this line, a user might be instructed to perform the treatment after bathing. To use the device 10, a user grasps the handle 12 and rakes the tines 18 against wart tissue to create a plurality of incisions, small troughs, or grooves in the tissue. The movement is preferably a rapid back and forth movement, similar to the rapid movement of a toothbrush during brushing. The sharpness and cutting depth of the tines 18 is selected so that the tines create the incisions in the relatively thick, tough, keratinous outer layer of the wart without causing noticeable bleeding. The tines 18 are preferably sufficiently long and sharp to penetrate the stratum corneum. The width 24 of the pad 14 is selected to allow a user to accurately pinpoint an area to be treated without also creating incisions is unaffected tissue. The width 24 is also sufficiently narrow to allow the device 10 to be used in hard to reach areas. The length 28 of the pad 14 is selected to allow a user to use long, smooth, slow, controlled strokes. The user continues the raking action for a desired period of time, typically a few seconds. The user may treat the affected area on a regular basis until the desired degree of tissue removal is obtained. The device 10 may also be used in combination with lotions or medicaments designed for wart removal to increase the effectiveness of those lotions or medicaments. Pyruvic acid is a preferred medicament, but it is understood that any number of lotions or medicaments may be used. In that regard, a user would rake the device 10 on the affected area to create a plurality of incisions and would then apply the medicament to the affected area. Creating incisions in the relatively thick, tough, keratinous tissue provides for better contact between the medicament and the tissue to be treated. This is particularly true if the incisions are deep enough to penetrate the stratum corneum.

The device 10 is best suited for use in connection with thick warts located on the palms of the hands, soles of the feet, and around toenails and fingernails. It is of course understood that the device may be used in to treat warts in other areas or to treat other conditions.

The device 10 and medicament may be sold together as a kit. In the past, physicians and patients have been understandably reluctant to have the patient perform self-treatment using a sharp cutting device. The present device makes self-treatment much more safe and practical. Still, the kit would preferably be sold by prescription only so that a physician could provide some counseling or training on proper techniques for using the device 10. Similarly, if sold by prescription only, the counseling or training offered by the physician would make it safer to provide a stronger, more concentrated medicament to the patient to further increase the effectiveness of the treatments.

Other modifications, changes, and substitutions are intended in the foregoing, and in some instances, some features of the invention will be employed without a corresponding use of other features. For example, the sloping surfaces 38a and 38b forming the point 40 at the upper edge of each tine 18 may extend over all or substantially all of the height 34 of the tine 18. Similarly, the tines 18 may be formed separately from or formed integrally with the base 16. The device 10 may also be used with or without an accompanying use of medicament. Further still, although the device 10 has been described as being used in connection with wart removal in a non-clinical setting, the device 10 may be used by physicians in a clinical setting and may be used to remove tissue other than wart tissue. It is understood that all measurements and quantitative information are given by way of example only and are not intended to limit the scope of the invention. Accordingly, it is appropriate that the appended claims be construed broadly and in a manner consistent with the scope of the invention.

What is claimed is:

1. A kit for treating warts, comprising:

a medicament, said medicament comprising pyruvic acid; and a device, said device comprising:

an elongate handle; and a pad affixed to said handle, said pad comprising a base and a plurality of tines extending upward from said base, said plurality of tines being arranged to form a plurality of columns and a plurality of rows, each of said plurality of tines having a tine height and having a tine width near where said tine meets said base, said tine height being not less than approximately twice said tine width.

2. A method of removing wart tissue, comprising:

(1) providing a device comprising a handle and a pad affixed to said handle, said pad comprising a base and a plurality of tines, each of said plurality of tines having a tine height and a tine width, said tine height being not less than approximately twice said tine width; and (2) raking said plurality of tines against wart tissue to create a plurality of incisions in said tissue.

3. The method of claim 2, wherein step (2) comprises raking said plurality of tines against said wart tissue to create said plurality of incisions in said tissue without causing noticeable bleeding.

4. The method of claim 2, further comprising:

after step (2), applying a medicament to said wart tissue.

5. The method of claim 4, wherein said medicament comprises pyruvic acid.

* * * * *